(12) United States Patent
Frassetto et al.

(10) Patent No.: US 9,546,130 B2
(45) Date of Patent: Jan. 17, 2017

(54) PROCESS FOR MANUFACTURING HALOACETAMIDES

(71) Applicant: BASF SE, Ludwigshafen (DE)

(72) Inventors: Timo Frassetto, Mannheim (DE); Volker Maywald, Ludwigshafen (DE); Michael Rack, Eppelheim (DE); Maximilian Dochnahl, Munich (DE); Bernd Wolf, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/902,890

(22) PCT Filed: Jun. 4, 2014

(86) PCT No.: PCT/EP2014/061591
§ 371 (c)(1),
(2) Date: Jan. 5, 2016

(87) PCT Pub. No.: WO2015/003858
PCT Pub. Date: Jan. 15, 2015

(65) Prior Publication Data
US 2016/0176805 A1    Jun. 23, 2016

(30) Foreign Application Priority Data
Jul. 12, 2013  (EP) ..................... 13176323

(51) Int. Cl.
C07C 231/02   (2006.01)
C07C 51/58    (2006.01)
C07C 231/00   (2006.01)

(52) U.S. Cl.
CPC ............. *C07C 231/02* (2013.01); *C07C 51/58* (2013.01); *C07C 231/00* (2013.01)

(58) Field of Classification Search
CPC ....... C07C 231/02; C07C 231/00; C07C 51/58
See application file for complete search history.

(56) References Cited

U.S. PATENT DOCUMENTS 9,365,495 B2 * 6/2016 Dochnahl ............ C07D 413/04
2030/0032836    2/2003 Gilles et al.

FOREIGN PATENT DOCUMENTS

| EP | 1719761 | 11/2006 |
|---|---|---|
| JP | 11080084 | 7/1997 |
| WO | WO 2006129100 | 12/2006 |

OTHER PUBLICATIONS

Niel et al, J. Med. Chem., vol. 42, pp. 2087-2104, 1999.*
Prabhakaran et al., "Synthesis and in vivo Evaluation of [<18>F]-4-[5-(4-methylphenyl)-3-(trifluoromethyl)-1H-pyrazole-1-yl]benzenesulfonamide as a PET Imaging Probe for COX-2 Expression," Bioorganic & Medicinal Chemistry, vol. 15, No. 4, (2007), pp. 1802-1807.
Morel et al., "Synthèse d'un nouveau monomère hydrofluorocarboxylique: Le difluoro-2,2-butène-3-oate d'éthyle," Tetrahedron, vol. 33, (1977), pp. 1445-1447.
Dolbier et al., "Syntheses of 2-(bromodifluoromethyl)benzoxazole and 5-(bromodifluoromethyl)-1,2,4-oxadiazoles," Journal of Fluorine Chemistry, vol. 95, Nos. 1-2, (1999), pp. 127-130.
Coe et al., "Polyfluoror-1,2-Epoxy Alkanes and Cycloalkanes," J. Fluorine Chemistry, vol. 27, (1985), pp. 71-84.
Rong et al., "1,1-Bis(dimethylamino)-2,2,2-trifluoroethane, a Readily-Available Precursor to the Novel Fluorinated Building Block 1,1-Bis(dimethylamino)-2,2-difluoroethane," J. Org. Chem., vol. 62, (1997), pp. 1576-1577.
International Search Report, issued in PCT/EP2014/061591, dated Jul. 7, 2014.
International Preliminary Report on Patentability, issued in PCT/EP2014/061591, dated Jan. 12, 2016.
European Search Report, issued in corresponding Application No. 13176323.7, dated Oct. 28, 2013.

* cited by examiner

*Primary Examiner* — Shailendra Kumar
(74) *Attorney, Agent, or Firm* — Brinks Gilson & Lione

(57) ABSTRACT

The present invention relates to a process for manufacturing haloacetamides of formula (I),

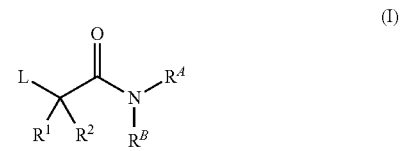

comprising
sub-step (a): reacting halones of formula (II) with oleum; followed by
sub-step (b): reacting the reaction mixture obtained in sub-step (a) with an amine of formula (IV) optionally in the presence of a base;
wherein the variables are defined according to the description.

8 Claims, No Drawings

PROCESS FOR MANUFACTURING HALOACETAMIDES

This application is a National Stage application of International Application No. PCT/EP2014/061591, filed Jun. 4, 2014. This application also claims priority under 35 U.S.C. §119 to European Patent Application No. 13176323.7, filed Jul. 12, 2013.

The invention relates to a process for manufacturing haloacetamides of formula (I), which are valuable intermediates in various chemical manufacturing processes.

JP 11080084 teaches a process for the preparation of halogenated acetic acid esters starting from haloalkanes.

Rong et al. (J. Org. Chem. 1997, 62, 1576-1577) discloses the synthesis of haloacetamides from the respective haloalkanes via the corresponding bis(dialkylamino)-alkenyles. This process involves several steps and also the use of n-butyllithium.

Coe et al. (J. Fluorine Chem. 1985, 27, 71-85) discloses a synthesis of haloacetamides from the epoxides of the pentamer and hexamer oligomers of tetrafluoroethylene via the corresponding halogenated ketone. This process requires pyrolysis conditions and suffers on low yields.

Dolbier et al. (J. Fluorine Chem. 1999, 95, 127-30) discloses a synthesis of haloacetamides from ethyl bromodifluoroacetate, which is an expensive starting material.

Hence, there is still room for improvement, specifically in view of economic and ecological aspects. Owing to the expense of some starting materials, long reaction times, complicated reaction steps and moderate yields, the known synthesis routes are not an option for an economic industrial preparation of the haloacetamides of formula (I).

Thus, it is an object of the present invention to provide an efficient process for manufacturing haloacetamides of formula (I), which is suitable for industrial scale application and proceeds from commercially readily available feedstocks.

Surprisingly it has been found that haloacetamides of formula (I) can be prepared by reacting halones of formula (II) with oleum, followed by reaction with amines of formula (III).

Accordingly, the present invention relates to a process for manufacturing haloacetamides of formula (I),

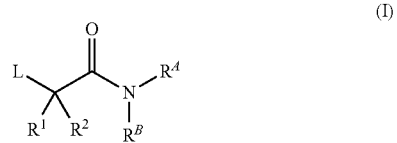

wherein
L is halogen;
$R^1$ is halogen;
$R^2$ is H or halogen;
$R^A$ is H, $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl,
wherein the phenyl and the benzyl ring independently of one another are unsubstituted or substituted with 1 to 5 substituents selected from the group consisting of halogen, $NO_2$, $C_1$-$C_6$-alkyl or $C_1$-$C_6$-alkoxy; and $R^B$ is $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl,
wherein the phenyl and the benzyl ring are independently of one another unsubstituted or substituted with 1 to 5 substituents selected from the group consisting of halogen, $NO_2$, $C_1$-$C_6$-alkyl or $C_1$-$C_6$-alkoxy;
or $R^A$ and $R^B$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;

comprising
sub-step (a): reacting halones of formula (II),

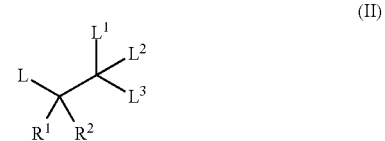

wherein L, $R^1$ and $R^2$ are defined as in formula (I); and $L^1$, $L^2$ and $L^3$ independently of one another are halogen; with oleum;
followed by
sub-step (b): reacting the reaction mixture obtained in sub-step (a) with an amine of formula (IV)

or a salt thereof,
wherein
$R^A$ is H, $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl,
wherein the phenyl and the benzyl ring independently of one another are unsubstituted or substituted with 1 to 5 substituents selected from the group consisting of halogen, $NO_2$, $C_1$-$C_6$-alkyl or $C_1$-$C_6$-alkoxy;
$R^B$ is $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl,
wherein the phenyl and the benzyl ring are independently of one another unsubstituted or substituted with 1 to 5 substituents selected from the group consisting of halogen, $NO_2$, $C_1$-$C_6$-alkyl or $C_1$-$C_6$-alkoxy;
or $R^A$ and $R^B$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;

optionally in the presence of a base.

The organic moieties mentioned in the definition of the variables according to the present invention, e.g. $R^1$, $R^2$, $R^A$ and $R^B$ are—like the term halogen—collective terms for individual enumerations of the individual group members.

The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, and $CH(CH_3)_2$ n-butyl, $CH(CH_3)$—$C_2H_5$, $CH_2$—CH$(CH_3)_2$ and $C(CH_3)_3$;

$C_1$-$C_6$-alkyl and also the $C_1$-$C_6$-alkyl moieties of $C_1$-$C_6$-cynaoalkyl, $C_1$-$C_6$-nitroalkyl, $C_1$-$C_6$-hydroxyalkyl, $C_1$-$C_6$-alkyoxy-$C_1$-$C_6$-alkyl, $C_3$-$C_6$-cycloalkyl-$C_1$-$C_4$-alkyl, amino-$C_1$-$C_6$-alkyl, ($C_1$-$C_6$-alkyl)amino-$C_1$-$C_6$-alkyl and di($C_1$-$C_6$-alkyl)amino-$C_1$-$C_6$-alkyl: $C_1$-$C_4$-alkyl as mentioned above, and also, for example, n-pentyl, 1-methylbutyl, 2-methylbutyl, 3-methylbutyl, 2,2-di methyl propyl, 1-ethylpropyl, n-hexyl, 1,1-dim-ethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-penta-fluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclo-pentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodo-pent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino and also the ($C_1$-$C_6$-alkyl)amino moieties of ($C_1$-$C_6$-alkyl)amino-$C_1$-$C_6$-alkyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethyl-propylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethyl-propylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methyl-ethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methyl-propyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)-N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methyl-propyl)amino, N-(1,1-dimethylethyl)-N-(1-methylpropyl)amino or N-(1,1-dimethylethyl)-N-(2-methylpropyl)amino;

di($C_1$-$C_6$-alkyl)amino and also the di($C_1$-$C_6$-alkyl)amino moieties of di($C_1$-$C_6$-alkyl)amino-$C_1$-$C_6$-alkyl: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethyl-propyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)-amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethyl-butyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methyl-pentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethyl-butyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)-amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

saturated or aromatic 3- to 6-membered ring optionally containing 1 to 3 additional heteroatoms selected from the group O, S and N:

a monocyclic, saturated or aromatic cycle having three to six ring members which comprises apart from one nitrogen atom and carbon atoms optionally additionally one to three heteroatoms selected from the group O, S and N, for example: 1-aziridinyl, 1-azetidinyl; 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl; 1-pyrrolyl, 1-pyrazolyl, 1-imidazolyl, 1,2,3-triazol-1-yl, 1,2,4-triazol-1-yl, 1-tetrazolyl; 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl.

The process of the invention comprises two sub-steps—a dehalo-oxygenation [sub-step (a)] and an amidation [sub-step (b)].

In the first part of the process according to the invention [sub-step (a)] the halones of formula (II) are reacted with oleum:

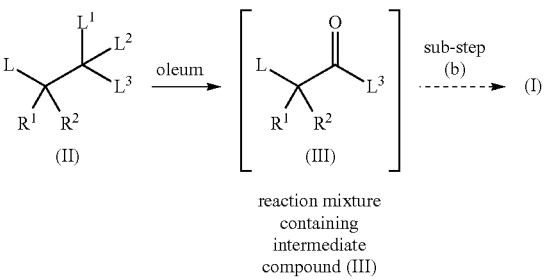

reaction mixture containing intermediate compound (III)

wherein the substituents are as herein defined.

The reaction of halones of formula (II) with oleum is usually carried out at from 20° C. to the boiling point of the reaction mixture, preferably from 20° C. to 95° C., particularly preferably from 20° C. to 85° C.

The reaction can be carried out at atmospheric pressure or under elevated pressure, if appropriate under an inert gas.

The oleum suitable for sub-step (a) according to the invention usually has a $SO_3$ content of up to 65%;
preferably of 25 to 65%;
particularly preferred of 40 to 65%;
especially preferred of 50 to 65%.

In one embodiment of the process according to the invention, the halones of formula (II) and the oleum are used in equimolar amounts.

In another embodiment of the process according to the invention the oleum is used in excess with regard to the halones of formula (II).

Preferably at least two equivalents of oleum with regard to the halones of formula (II) are used. Particularly preferred the molar ratio of the halone of formula (II) to the oleum is in the range from 5:1 especially preferred 2:1.

The reaction may in principle be carried out in substance without any additional solvent. However, it is also possible to react the halones of formula (II) with the oleum in an organic solvent. Suitable in principle are all solvents which are capable of dissolving the halones formula (II) and the oleum at least partly and preferably fully under reaction conditions.

Preferably the reaction the halones of formula (II) with the oleum is carried out in the absence of any additional solvent.

In one embodiment of the process according to the invention the reaction of the halones of formula (II) with oleum [sub-step (a)] is carried out in the presence of a catalyst.

Suitable catalysts are metals (e.g. Fe, Zn, Mn, Co, Ni or Cu), their corresponding oxides (e.g. FeO, $Fe_2O_3$, ZnO, $MnO_2$, NiO, CuO, $Cu_2O$) and salts (e.g. $Fe_2(SO_4)_3$, $CuSO_4$, $Cu_2SO_4$, $ZnSO_4$, $NiSO_4$);
preferred are Fe, Zn, Mn, Co, Ni or Cu, their corresponding oxides and sulfates;
particularly preferred are Fe, Zn, Mn, Co, Ni or Cu and their corresponding oxides;
especially preferred are Fe, FeO, $Fe_2O_3$, ZnO, $MnO_2$, NiO, CuO and $Cu_2O$;
more preferred is $Fe_2O_3$.

In another embodiment of the process according to the invention the reaction of the halones of formula (II) with oleum [sub-step (a)] is carried out in the absence of a catalyst.

Such embodiment is preferred.

For the reaction, the halones of formula (II) and the oleum and optionally the catalyst can be brought into contact in any way per se. This means that the reaction partners may be introduced into the reaction vessel and reacted separately, simultaneously or successively.

For example, the halones of formula (II), the oleum, and optionally the catalyst, may be initially charged in a reaction vessel, and then the desired reaction conditions may be attained.

In one embodiment of the process according to the invention, the oleum is initially charged in a reaction vessel, and subsequently the halones of formula (II), and optionally the catalyst, are added into the reaction vessel.

In another embodiment of the process according to the invention, the halones of formula (II) and optionally the catalyst are initially charged in a reaction vessel, and subsequently the oleum is added into the reaction vessel.

In a further embodiment of sub-step (a) of the process according to the invention, the oleum and the halones of formula (II), and optionally the catalyst, are reacted in a pressure-vessel. After completion or partial completion of sub-step (a) of the process according to the invention, the reaction mixture is allowed to cool down followed by pressure release and sub-step (b).

In a further embodiment of the process according to the invention, the oleum is initially charged in a pressure-vessel, and subsequently the halones of formula (II), and optionally the catalyst, are added into the pressure-vessel, to allow the reaction of step (a) taking place in a closed system.

In a further embodiment of the process according to the invention, the halones of formula (II) and optionally the catalyst are initially charged in a pressure-vessel, and subsequently the oleum is added into the closed pressure-vessel, to allow the reaction of step (a) taking place in a system.

The end of the reaction can easily be determined by the skilled worker by means of routine methods.

In one embodiment of the process according to the invention, the reaction mixture obtained in sub-step (a) is not worked up, but the intermediate of formula (III) is directly distilled off the reaction mixture obtained in sub-step (a), and the distillate obtained therefrom [containing the intermediate of formula (III)] is transferred directly into the reactor used for sub-step (b).

Such embodiment is preferred.

Appropriately, the reaction of the halones of formula (II) with the oleum is carried out in an apparatus which is equipped with at least one distillation or rectification apparatus, for example a distillation column, which firstly allows the intermediate of formula (III) to be distilled off and simultaneously enables removal and recycling of halone of formula (II) distilled off with the intermediate of formula (III).

In the second part of the process according to the invention [sub-step (b)] the intermediate of formula (III) obtained from sub-step (a), or the distillate obtained from sub-step (a) containing intermediate compound (III), is reacted with an amine of formula (IV) or a salt thereof, optionally in the presence of a base:

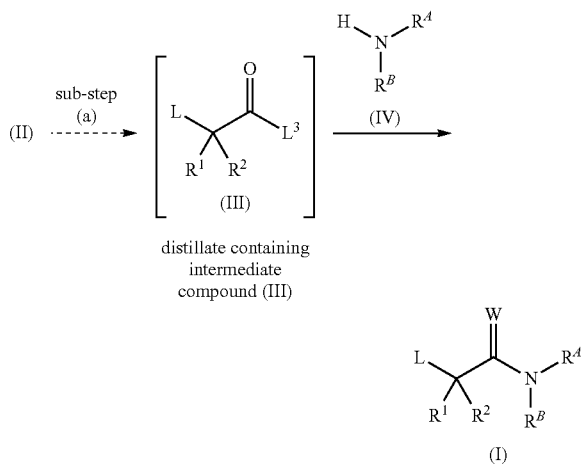

wherein the substituents are as herein defined.

Sub-step (b) [the reaction of the intermediate of formula (III) obtained from sub-step (a), or the distillate obtained from sub-step (a) containing intermediate compound (III), with the amine of formula (IV) or a salt thereof] is usually carried out at from −50° C. to the boiling point of the reaction mixture, preferably from −20° C. to 50° C., particularly preferably from −15° C. to 25° C.

Sub-step (b) can be carried out at atmospheric pressure or under elevated pressure, if appropriate under an inert gas, continuously or batchwise.

In one embodiment of the process according to the invention, the amount of amines of formula (IV) or a salt thereof used in sub-step (b) is in excess with regard to the halones of formula (II) used in sub-step (a) before.

In another embodiment of the process according to the invention, the amount of amines of formula (IV) or a salt thereof used in sub-step (b) is equimolar to the amount of halones of formula (II) used in sub-step (a) before.

Preferably the molar ratio of the halones of formula (II) to the amines of formula (IV) or a salt thereof is in the range from 1:5 to 1:4, preferably 1:4.5 to 1:4, especially preferred 1:3.3 to 1:2.0, also especially preferred 1:2.5.

Sub-step (b) may in principle be carried out in substance. However, preferably the intermediate of formula (III) or the distillate obtained from sub-step (a) containing intermediate compound (III)), and the amine of formula (IV) or a salt thereof are reacted in an organic solvent.

Suitable in principle are all solvents which are capable of dissolving the intermediate of formula (III), the reaction mixture or the distillate, both obtained from sub-step (a) and containing the intermediate of formula (III), and the amine of formula (IV) or a salt thereof, at least partly and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene, mesitylene; halogenated hydrocarbons such as dichloromethane, 1,2-dichloroethane, chloroform, carbon tetrachloride, chlorobenzene, dichlorobenzene, fluorobenzene and benzotrifluoride; ethers such as diethyl ether, diisopropyl ether, tert.-butyl methylether (TBME), cyclopentyl methyl ether, tert.-amyl methyl ether, dioxane, anisole, methyltetrahydrofurane and tetrahydrofuran (THF); nitriles such as acetonitrile, benzonitrile and propionitrile; ketones such as acetone, methyl ethyl ketone, diethyl ketone, methyl isobutyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

The term solvent as used herein also includes mixtures of two or more of the above compounds.

Preferred solvents are ethers as defined above, preferably THF, or mixtures of ethers, preferably THF, as defined with other solvents as defined above.

More preferred solvents are mixtures of ethers, preferably THF, as defined with other solvents as defined above.

In one embodiment of the invention, the solvents used in sub-step (b) preferably are ethers as defined above, or mixtures of ethers as defined with other solvents as defined above, more preferably mixtures of ethers as defined with other solvents as defined above.

Such embodiment is especially preferred in case substituent L within the halones of formula (II) is bromine.

The amines of formula (IV) as described herein can also be employed in the form of their salts. Suitable are, in general, the salts of those cations and the acid addition salts of those acids whose cations and anions, respectively, have no adverse effect on the reaction.

Preferred cations are the ions further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl) ammonium (diolamine salt), tris(2-hydroxyethyl) ammonium (trolamine salt), tris(2-hydroxypropyl) ammonium, benzyltrimethylammonium, benzyltriethylammonium, N,N,N-trimethylethanolammonium (choline salt); furthermore phosphonium ions; sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine.

Especially preferred the amines of formula (IV) as described herein are employed in form of their ammonium salts.

Anions of useful acid addition salts are primarily halogenides such as chloride, bromide, fluoride, iodide, hydrogensulfate, alkylsulfates such as methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Especially preferred the amines of formula (IV) as described herein are employed in form of their halogenides and sulfates,
particular preference is given to the chlorine and the sulphate of the amines of formula (IV), more preference is given to the ammonium chlorine of the amines of formula (IV) and the ammonium sulphate of the amines of formula (IV).

The term "a salt" or "salts" as used herein also includes mixtures of two or more, preferably two of the above different salts. Particular preference is given to the use of one salt.

In one embodiment of sub-step (b) of the invention the amines of formula (IV) are employed.

In another embodiment of sub-step (b) of the invention a salt of the amines of formula (IV) is employed.

Sub-step (b) is optionally carried out in the presence of a base.

If a salt of the amines of formula (IV) is used, the addition of a base in sub-step (b) according to the invention is necessary.

If the amines of formula (IV) are used as such, the addition of a base in sub-step (b) according to the invention is not necessary.

Examples of suitable bases include nitrogen-containing bases such as tertiary amines e.g. tri-$C_1$-$C_6$-alkylamines, for example triethylamine, trimethylamine, N-ethyldiisopropylamine, and N-methylpiperidine, N-methylmorpholine, pyridine, substituted pyridines such as collidine, lutidine, picolines and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are $C_1$-$C_6$-alkylaminesn and pyridins as defined above.

Especially preferred bases are $C_1$-$C_6$-alkylaminesn and pyridins as defined above.

The term "base" as used herein also includes mixtures of two or more, preferably two of the above compounds. Particular preference is given to the use of one base.

The bases are generally employed in equimolar amounts with regard to the salt of the amines of formula (IV), however they can also be employed in excess or, if appropriate, be used as solvent.

Preferably the bases are employed in equimolar amounts with regard to the salt of the amines of formula (IV).

For sub-step (b) of the reaction, the intermediate of formula (III) obtained from sub-step (a), or the distillate obtained from sub-step (a) containing intermediate compound (III), and the amine of formula (IV) or a salt thereof, can be brought into contact in any way per se.

This means that the reaction partners may be introduced into the reaction vessel and reacted separately, simultaneously or successively.

For example the intermediate of formula (III) obtained from sub-step (a), or the distillate obtained from sub-step (a) containing intermediate compound (III), and the amine of formula (IV) may be initially charged in a reaction vessel, if appropriate with the desired solvent, and then the desired reaction conditions may be attained.

However, it is also possible to introduce the majority or entirety of the intermediate of formula (III) obtained from sub-step (a), or the distillate obtained from sub-step (a) containing intermediate compound (III), and subsequently adding the amine of formula (IV), if appropriate in a solvent, under reaction conditions, into the reaction vessel.

In one embodiment of the process according to the invention, the amine of formula (III) is initially charged in a reaction vessel, if appropriate with the desired solvent, and subsequently the intermediate of formula (III) obtained from sub-step (a), or the distillate obtained from sub-step (a) containing intermediate compound (III), is added, more preferably is added a little at a time, into the reaction vessel.

The end of the reaction can easily be determined by the skilled worker by means of routine methods.

After completion or partial completion of the reaction, the reaction mixture can be worked up by the methods customary for the purpose by means of standard techniques. Examples thereof include aqueous work-up, evaporation of solvents and/or other volatile compounds. These methods can also be combined with each other.

In general the solvent used is removed by customary methods, distillatively for example.

For further purification it is possible to employ the typical methods such as distillation, rectification, crystallization, precipitation (for example by addition of an apolar solvent such as pentane, cyclohexane, heptane or toluene, or mixtures of said solvents) or chromatography.

The preferred embodiments of the invention mentioned herein below have to be understood as being preferred either independently from each other or in combination with one another.

According to a preferred embodiment of the invention preference is also given to the preparation of those haloacetamides of formula (I),

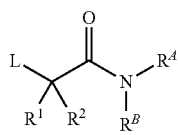
(I)

wherein the variables, either independently of one another or in combination with one another, have the following meanings:

L is preferably Cl, Br or I;
   particularly preferred Cl or Br;
   especially preferred Br;
$R^1$ is preferably Cl or F;
   particularly preferred F;
$R^2$ is preferably H, Cl or F;
   particularly preferred H or F;
   especially preferred H;
   is also preferably halogen;
   particularly preferred F or Cl;
   especially preferred F;
preferably
$R^A$ is H, $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
   wherein the phenyl and the benzyl ring are independently of one another unsubstituted or substituted with 1 to 3 substituents selected from the group consisting of halogen, $C_1$-$C_6$-alkyl or $C_1$-$C_6$-alkoxy;
$R^B$ is $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
   wherein the phenyl and the benzyl ring are independently of one another unsubstituted or substituted with 1 to 3 substituents selected from the group consisting of halogen, $C_1$-$C_6$-alkyl or $C_1$-$C_6$-alkoxy; or
$R^A$ and $R^B$ preferably together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;
particularly preferred
$R^A$ is H, $C_1$-$C_4$-alkyl, $C_1$-$C_4$-hydroxyalkyl, $C_1$-$C_6$-alkoxy-$C_1$-$C_4$-alkyl or benzyl,
   wherein the benzyl ring is unsubstituted or substituted by 1 to 3 substituents selected from the group consisting of halogen, $C_1$-$C_4$-alkyl or $C_1$-$C_4$-alkoxy, especially preferred the benzyl ring is unsubstituted;
$R^B$ is $C_1$-$C_4$-alkyl, $C_1$-$C_4$-hydroxyalkyl, $C_1$-$C_6$-alkoxy-$C_1$-$C_4$-alkyl or benzyl,
   wherein the benzyl ring is unsubstituted or substituted by 1 to 3 substituents selected from the group consisting of halogen, $C_1$-$C_4$-alkyl or $C_1$-$C_4$-alkoxy,
   especially preferred the benzyl ring is unsubstituted; or
$R^A$ and $R^B$ together with the N atom which they are attached to, represent a saturated 5- to 6-membered ring, optionally containing 1 additional oxygen atom, with the ring optionally being substituted with 1 to 2 $C_1$-$C_6$-alkyl substituents;
especially preferred
$R^A$ is H, $C_1$-$C_4$-alkyl or $C_1$-$C_6$-alkoxy-$C_1$-$C_4$-alkyl; and
$R^B$ is $C_1$-$C_4$-alkyl or $C_1$-$C_6$-alkoxy-$C_1$-$C_4$-alkyl;
more preferred
$R^A$ is H or $C_1$-$C_4$-alkyl; and
$R^B$ is $C_1$-$C_4$-alkyl;
also more preferred $R^A$ and $R^B$ independently of one another are $C_1$-$C_4$-alkyl.

Particular preference is given to the haloacetamides of formula (Ia) (corresponds to haloacetamides of formula (I) wherein $R^1$ and $R^2$ are F),

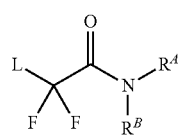

(Ia)

wherein the variables $R^A$, $R^B$ and L have the meanings, in particular the preferred meanings, as defined above;

special preference is given to the haloacetamides of formulae (Ia.1) to (Ia.24) of table A listed below, in which the variables $R^A$, $R^B$ and L together have the meanings given in one row of Table A (haloacetamides of formulae (Ia.1) to (Ia.24); and where the definitions of the variables $R^A$, $R^B$ and L are of particular importance for the process and the compounds according to the invention not only in combination with one another but in each case also on their own:

TABLE A

| no. | L | $R^A$ | $R^B$ |
|---|---|---|---|
| III.1 | Cl | H | $CH_3$ |
| III.2 | Cl | H | $C_2H_5$ |
| III.3 | Cl | H | $CH(CH_3)_2$ |
| III.4 | Cl | $CH_3$ | $CH_3$ |
| III.5 | Cl | $CH_3$ | $C_2H_5$ |
| III.6 | Cl | $CH_3$ | $CH(CH_3)_2$ |
| III.7 | Cl | $CH_2CH_3$ | $CH_2CH_3$ |
| III.8 | Cl | —$CH_2$—$CH_2$—$CH_2$—$CH_2$— | |
| III.9 | Cl | —$CH_2$—$CH_2$—$CH_2$—$CH_2$—$CH_2$— | |
| III.10 | Cl | —$CH_2$—$CH_2$—O—$CH_2$—$CH_2$— | |
| III.11 | Cl | —$CH_2$—$CH_2$—$N(CH_3)$—$CH_2$—$CH_2$— | |
| III.12 | Cl | —$CH_2$—$CH(CH_3)$—O—$CH(CH_3)$—$CH_2$— | |
| III.13 | Br | H | $CH_3$ |
| III.14 | Br | H | $C_2H_5$ |
| III.15 | Br | H | $CH(CH_3)_2$ |
| III.16 | Br | $CH_3$ | $CH_3$ |
| III.17 | Br | $CH_3$ | $C_2H_5$ |
| III.18 | Br | $CH_3$ | $CH(CH_3)_2$ |
| III.19 | Br | $CH_2CH_3$ | $CH_2CH_3$ |
| III.20 | Br | —$CH_2$—$CH_2$—$CH_2$—$CH_2$— | |
| III.21 | Br | —$CH_2$—$CH_2$—$CH_2$—$CH_2$—$CH_2$— | |
| III.22 | Br | —$CH_2$—$CH_2$—O—$CH_2$—$CH_2$— | |
| III.23 | Br | —$CH_2$—$CH_2$—$N(CH_3)$—$CH_2$—$CH_2$— | |
| III.24 | Br | —$CH_2$—$CH(CH_3)$—O—$CH(CH_3)$—$CH_2$— | |

Especially preferred are the haloacetamides of formulae (III.13) to (III.24) as defined above, more preferred the haloacetamides of formulae (III.13), (III.16), (III.17), (III.18) as defined above;

very particular preferred is the haloacetamide of formula (III.16) as defined above.

With respect to the substituents within the halones of formula (II) necessary for the process according to the invention,

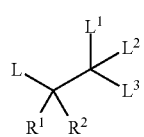

(II)

the particularly preferred embodiments of the halones of formula (II) correspond, either independently of one another or in combination with one another, to those of the variables of L, $R^1$, and $R^2$ of formula (I); and $L^1$ is fluorine or chlorine;
preferably fluorine;
also preferably chlorine;
$L^2$ is chlorine or bromine;
preferably chlorine;
also preferably bromine;
$L^3$ is fluorine.

Particular preference is given to the halones of formula (II.a), which correspond to halones of formula (II) wherein $R^1$ and $R^2$ are F:

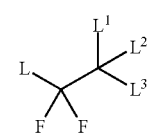

(II.a)

wherein the variables L, $L^1$, $L^2$ and $L^3$ have the meanings, in particular the preferred meanings, as defined above; special preference is given to the halones of formulae (II.a.1) to (II.a.8) of Table B listed below, in which the variables L, $L^1$, $L^2$ and $L^3$ together have the meanings given in one row of Table B [halones of formulae (II.a.1) to (II.a.8]; and where the definitions of the variables L, $L^1$, $L^2$ and $L^3$ are of particular importance for the process according to the invention not only in combination with one another but in each case also on their own:

TABLE B

| No. | L | $L^1$ | $L^2$ | $L^3$ |
|---|---|---|---|---|
| II.a.1 | Cl | F | Cl | F |
| II.a.2 | Cl | F | Br | F |
| II.a.3 | Cl | Cl | Cl | F |
| II.a.4 | Cl | Cl | Br | F |
| II.a.5 | Br | F | Cl | F |
| II.a.6 | Br | F | Br | F |
| II.a.7 | Br | Cl | Cl | F |
| II.a.8 | Br | Cl | Br | F |

Special preference is given to the halones of formulae (II.a.1), (II.a.6) and (II.a.8) as defined above;
especially preferred are the halones of formulae (II.a.6) and (II.a.8) as defined above.

The halones of formula (II) required for the preparation of haloacetamides of formula (I) are known from the literature (e.g. EP 1418163; U.S. Pat. No. 4,748,285) or they can be prepared in accordance with the literature cited or are commercially available.

With respect to the variables within the amines of formula (IV),

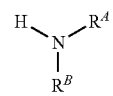

(IV)

the particularly preferred embodiments of the amines of formula (IV) correspond, either independently of one another or in combination with one another, to those of the variables of $R^A$ and $R^B$ of formula (I).

Particular preference is given to the amines of of formulae (IV.1) to (IV.12) of Table C listed below, in which the variables $R^A$ and $R^B$ together have the meanings given in one row of Table C (amines of formulae (III.1) to (III.11)); and where the definitions of the variables $R^A$ and $R^B$ are of particular importance for the process according to the invention not only in combination with one another but in each case also on their own:

TABLE C

| no. | $R^A$ | $R^B$ |
|---|---|---|
| IV.1 | H | $CH_3$ |
| IV.2 | H | $C_2H_5$ |
| IV.3 | H | $CH(CH_3)_2$ |
| IV.4 | $CH_3$ | $CH_3$ |
| IV.5 | $CH_3$ | $C_2H_5$ |
| IV.6 | $CH_3$ | $CH(CH_3)_2$ |
| IV.7 | $CH_2CH_3$ | $CH_2CH_3$ |
| IV.8 | —$CH_2$—$CH_2$—$CH_2$—$CH_2$— | |
| IV.9 | —$CH_2$—$CH_2$—$CH_2$—$CH_2$—$CH_2$— | |
| IV.10 | —$CH_2$—$CH_2$—O—$CH_2$—$CH_2$— | |
| IV.11 | —$CH_2$—$CH_2$—N($CH_3$)—$CH_2$—$CH_2$— | |
| IV.12 | —$CH_2$—$CH_2$—$CH_2$—$CH_2$— | |

Especially preferred are the amines of formulae (IV.1), (IV.4), (IV.5), (IV.6) as defined above; more preferred is the amine of formula (IV.4) as defined above.

The amines of formula (IV) required for the preparation of haloacetamides of formula (I) are commercially available.

The invention is illustrated by the following examples without being limited thereto or thereby.

EXAMPLES

1. Preparation of 2-bromo-2,2-difluoro-N,N-dimethyl-acetamide

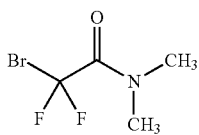

Example 1.1

40.0 g (0.14 mol) 1,2-dibromo-1-chloro-1,2,2-trifluoroethane, Freon 113B2 (97%) were placed in a 250 mL 4-necked flask equipped with a flexible Teflon tube connected with a second 500 mL reactor filled with a pre-cooled solution (−12° C.) of dimethylamine in THF (2.0 M, 250 mL) Oleum (65%, 34.6 g, 0.28 mol) was added to the Freon 113B over the course of 15 min at 22 to 24° C.

After some initiation period, the exothermic reaction slowly started which could be detected by the occurrence of brown fumes and the condensation of a colorless liquid at the cold parts of the flask. The reaction temperature was kept at 24° C. for two hours. Thereafter, the temperature was increased to 80° C. over the course of 6 h. The reaction mixture was kept at that temperature overnight.

Afterwards, the mixture was heated to 130° C. and the remainder distilled off.

The mixture in the second reactor was rectified over a 10 cm Vigreux column. The first fraction was distilled off under normal pressure and consisted of THF and low boiling side components.

The residue was distilled under reduced pressure (20-5 mbar) at 80-135° C. The first fraction was obtained as a colorless liquid (25.9 g; yield: 77%; purity: >85%)

Example 1.2

120.0 g (0.42 mol) 1,2-dibromo-1-chloro-1,2,2-trifluoroethane, Freon 113B2 (97%) were placed in a 500 mL Hastelloy C pressure reactor equipped with a flexible Teflon tube connected with a second 1 L reactor containing a pre-cooled solution (−12° C.) of dimethylamine in THF (2.0 M, 526 mL). Oleum (65%, 88.2 g, 0.72 mol) was added to the Freon 113B at −10° C. The pressure reaction was heated to 60° C. The reaction temperature was kept at 60° C. for two hours. A pressure of 5.5 bar was reached during the reaction. Thereafter, the pressure reactor was cooled to 15° C. and the pressure was released over the Teflon tube to the second reactor.

Afterwards, the pressure reactor was heated to 130° C. and the remainder distilled off. The mixture in the second reactor was rectified over a 10 cm Vigreux column. The first fraction was distilled off under normal pressure and consists of THF and low boiling side components. The residue was distilled under reduced pressure (20-5 mbar) at 80-135° C. The first fraction was obtained as a colorless liquid (100.5 g; yield: 90.1%; purity: 76.3%).

Example 1.3

120.0 g (0.42 mol) 1,2-dibromo-1-chloro-1,2,2-trifluoroethane, Freon 113B2 (97%) were placed in a 500 mL Hastelloy C pressure reactor equipped with a flexible Teflon tube connected with a second 1 L reactor containing a pre-cooled solution (←12° C.) of dimethylamine in THF (2.0 M, 526 mL). Oleum (65%, 88.2 g, 0.72 mol) was added to the Freon 113B at −10° C. The pressure reaction was heated to 50° C. The reaction temperature was kept at 50° C. for four hours. A pressure of 4.0 bar was reached during the reaction. Thereafter, the pressure reactor was cooled to 15° C. and the pressure was released over the Teflon tube to the second reactor.

Afterwards, the pressure reactor was heated to 130° C. and the remainder distilled off.

The mixture in the second reactor was rectified over a 10 cm Vigreux column. The first fraction was distilled off under normal pressure and consists of THF and low boiling side components. The residue was distilled under reduced pressure (20-5 mbar) at 80-135° C. The first fraction was obtained as a colorless liquid (97.8 g; yield: 87.8%; purity: 76.4%)

Example 1.4

120.0 g (0.42 mol) 1,2-dibromo-1-chloro-1,2,2-trifluoroethane, Freon 113B2 (97%) were placed in a 500 mL Hastelloy C pressure reactor equipped with a flexible Teflon tube connected with a second 1 L reactor containing a pre-cooled solution (←12° C.) of dimethylamine in THF (2.0 M, 526 mL). Oleum (65%, 88.2 g, 0.72 mol) was added to the Freon 113B at −10° C. The pressure reaction was heated to 40° C. The reaction temperature was kept at 40° C. for 10 h. A pressure of 3.6 bar was reached during the reaction. Thereafter, the pressure reactor was cooled to 15° C. and the pressure was released over the Teflon tube to the second reactor.

Afterwards, the pressure reactor was heated to 130° C. and the remainder distilled off.

The mixture in the second reactor was rectified over a 10 cm Vigreux column. The first fraction was distilled off under normal pressure and consists of THF and low boiling side components. The residue was distilled under reduced pressure (20-5 mbar) at 80-135° C. The first fraction was obtained as a colorless liquid (99.0 g; yield: 87.0%; purity: 74.8%)

Example 1.5

120.0 g (0.42 mol) 1,2-dibromo-1-chloro-1,2,2-trifluoroethane, Freon 113B2 (97%) were placed in a 500 mL Hastelloy C pressure reactor equipped with a flexible Teflon tube connected with a second 1 L reactor containing a pre-cooled solution (←−12° C.) of dimethylamine in 1,2-dichloroethane (2.0 M, 526 mL). Oleum (65%, 88.2 g, 0.72 mol) was added to the Freon 113B at −10° C. The pressure reaction was heated to 50° C. The reaction temperature was kept at 50° C. for 4 h. A pressure of 4.4 bar was reached during the reaction. Thereafter, the pressure reactor was cooled to 15° C. and the pressure was released over the Teflon tube to the second reactor.

Afterwards, the pressure reactor was heated to 130° C. and the remainder distilled off. The mixture in the second reactor was rectified over a 10 cm Vigreux column. The first fraction was distilled off under normal pressure and consists of THF and low boiling side components. The residue was distilled under reduced pressure (20-5 mbar) at 80-135° C. The first fraction was obtained as a colorless liquid (81.2 g; yield: 75.9%; purity: 79.6%).

Example 1.6

120.0 g (0.42 mol) 1,2-dibromo-1-chloro-1,2,2-trifluoroethane, Freon 113B2 (97%) were placed in a 500 mL Hastelloy C pressure reactor equipped with a flexible Teflon tube connected with a second 1 L reactor containing a pre-cooled solution (←−12° C.) of dimethylamine in diethylether (2.0 M, 540 mL). Oleum (65%, 88.2 g, 0.72 mol) was added to the Freon 113B at −10° C. The pressure reaction was heated to 50° C. The reaction temperature was kept at 50° C. for 4 h. A pressure of 4.4 bar was reached during the reaction. Thereafter, the pressure reactor was cooled to 15° C. and the pressure was released over the Teflon tube to the second reactor.

Afterwards, the pressure reactor was heated to 130° C. and the remainder distilled off.

The mixture in the second reactor was rectified over a 10 cm Vigreux column. The first fraction was distilled off under normal pressure and consists of THF and low boiling side components. The residue was distilled under reduced pressure (20-5 mbar) at 80-135° C. The first fraction was obtained as a colorless liquid (85.3 g; yield: 78.6%; purity: 78.4%).

Example 1.7

20.0 g (0.074 mol) 1,2-dibromo-1-chloro-1,2,2-trifluoroethane, Freon 113B2 (97%) were placed in a 4-necked flask with a flexible Teflon tube connected with a second 250 L reactor containing a pre-cooled solution (←−12° C.) of 12.0 g (0.148 mol) dimethylamine.HCl and 40 ml (0.296 mol) triethylamine in dichloromethane (400 mL). Oleum (50%, 14.8 g, 0.092 mol) was added to the Freon 113B at −10° C. After some initiation period, the exothermic reaction slowly started which could be detected by the occurrence of brown fumes and the condensation of a colorless liquid at the cold parts of the flask. The reaction temperature was increase to 80° C. and kept at 80° C. for 20 hours. Thereafter, the content of the second reactor was washed three-times with 100 mL water, the organic phase was dried over MgSO4. Afterwards the solvent was evaporated under reduced pressure.

The residue was distilled under reduced pressure (20-5 mbar) at 80-135° C. The first fraction was obtained as a colorless liquid (11.1 g; yield: 74.2%).

The invention claimed is:

1. A process for manufacturing haloacetamides of formula (I),

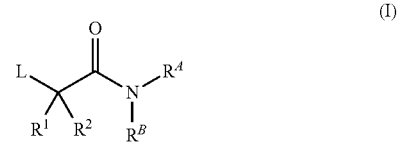

wherein
L is halogen;
$R^1$ is halogen;
$R^2$ is H or halogen;
$R^A$ is selected from the group consisting of H, $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl,
  wherein the phenyl and the benzyl ring independently of one another are unsubstituted or substituted with 1 to 5 substituents selected from the group consisting of halogen, $NO_2$, $C_1$-$C_6$-alkyl and $C_1$-$C_6$-alkoxy; and
$R^B$ is selected from the group consisting of $C_1$-$C_6$-alkyl, $C_2$-$C_6$-alkenyl, $C_2$-$C_6$-alkynyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl,
  wherein the phenyl and the benzyl ring are independently of one another unsubstituted or substituted with 1 to 5 substituents selected from the group consisting of halogen, $NO_2$, $C_1$-$C_6$-alkyl and $C_1$-$C_6$-alkoxy;
or $R^A$ and $R^B$ together with the N atom which they are attached to, represent a saturated or aromatic 3- to 6-membered ring, optionally containing 1 to 3 additional heteroatoms selected from the group consisting of O, S and N, with the ring optionally being substituted with 1 to 3 $C_1$-$C_6$-alkyl substituents;
comprising
sub-step (a): reacting halones of formula (II),

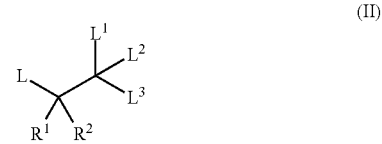

wherein L, $R^1$ and $R^2$ are defined as in formula (I);
$L^1$ and $L^2$ independently of one another are halogen; and
$L^3$ is fluorine;
with oleum;

followed by
sub-step (b): reacting the reaction mixture obtained in sub-step (a) with an amine of formula (IV)

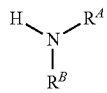

or a salt thereof,
wherein
$R^A$ is selected from the group consisting of H, $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl,
  wherein the phenyl and the benzyl ring independently of one another are unsubstituted or substituted with 1 to 5 substituents selected from the group consisting of halogen, $NO_2$, $C_1$-$C_6$-alkyl and $C_1$-$C_6$-alkoxy;
$R^B$ is selected from the group consisting of $C_1$-$C_6$-alkyl, $C_2$-$C_6$-alkenyl, $C_2$-$C_6$-alkynyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl,
  wherein the phenyl and the benzyl ring are independently of one another unsubstituted or substituted with 1 to 5 substituents selected from the group consisting of halogen, $NO_2$, $C_1$-$C_6$-alkyl and $C_1$-$C_6$-alkoxy;
or $R^A$ and $R^B$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;
optionally in the presence of a base.

2. The process of claim 1, wherein
$R^A$ is H, $C_1$-$C_4$-alkyl or $C_1$-$C_6$-alkoxy-$C_1$-$C_4$-alkyl; and
$R^B$ is $C_1$-$C_4$-alkyl or $C_1$-$C_6$-alkoxy-$C_1$-$C_4$-alkyl.

3. The process of claim 1, wherein sub-step (a) is carried out in the absence of any additional solvent.

4. The process claim 1, wherein in sub-step (a) the halones of formula (II) are initially charged in a reaction vessel and subsequently the oleum is added into the reaction vessel.

5. The process of claim 1, wherein in sub-step (a) the oleum and the halones of formula (II) are reacted in a pressure-vessel.

6. The process of claim 1, wherein the intermediate of formula (III)

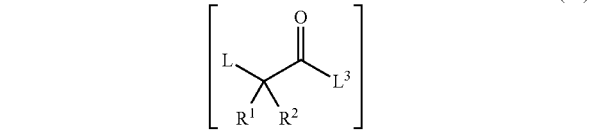

wherein L, $R^1$, $R^2$ and $L^3$ are defined as in claim 1;
obtained in sub-step (a) is directly distilled off the reaction mixture obtained in sub-step (a), and transferred directly into the reactor used for sub-step (b).

7. The process of claim 1, wherein sub-step (b) is carried out in an additional solvent selected from ethers, or mixtures of ethers with other solvents selected from the group consisting of aliphatic hydrocarbons, aromatic hydrocarbons, halogenated hydrocarbons, nitriles, ketones and dipolar aprotic solvents.

8. The process of claim 1, wherein in sub-step (b) the amines of formula (IV) are employed.

* * * * *